United States Patent [19]

Siclari et al.

[11] 4,177,214

[45] Dec. 4, 1979

[54] PROCEDURE FOR THE PREPARATION OF SATURATED AND UNSATURATED DIALDEHYDES

[75] Inventors: Francesco Siclari, Barlassina; Pietro P. Rossi, Garlasco; Cesare Guaita, Tradate; Vito L'Acqua, Milan, all of Italy

[73] Assignee: Snia Viscosa Societa' Nazionale Industria Applicazioni Viscosa S.p.A., Milan, Italy

[21] Appl. No.: 865,248

[22] Filed: Dec. 28, 1977

[30] Foreign Application Priority Data

Dec. 29, 1976 [IT] Italy ................. 30939 A/76

[51] Int. Cl.$^2$ ............................................. C07C 45/22
[52] U.S. Cl. ................................................. 260/601 R
[58] Field of Search ................................... 260/601 R

[56] References Cited

U.S. PATENT DOCUMENTS

| | | | |
|---|---|---|---|
| 2,854,459 | 9/1958 | Knowles | 260/339 |
| 2,888,485 | 5/1959 | Bailey | 260/523 |
| 3,637,721 | 1/1972 | Pappas | 260/601 R |
| 3,856,833 | 12/1974 | Siclari et al. | 260/601 R |
| 3,862,142 | 1/1975 | Story et al. | 260/601 R |

FOREIGN PATENT DOCUMENTS

| | | | |
|---|---|---|---|
| 998227 | 8/1973 | Italy | 260/601 R |
| 709450 | 5/1954 | United Kingdom | 260/601 R |

OTHER PUBLICATIONS

Lycan et al., "J. Amer. Chem. Soc.", vol. 51, pp. 625-629, (1929).
Henne et al., "J. Amer. Chem. Soc.", vol. 65, pp. 752-754, (1943).
Chem. Zento., (1959), p. 763.
Chem. Zentr., (1969), vol. 18, p. 1233.

*Primary Examiner*—Werren B. Lone
*Attorney, Agent, or Firm*—Burgess, Ryan and Wayne

[57] ABSTRACT

There is described a procedure for preparing unsaturated or saturated $\alpha,\omega$-dialdehydes, wherein the monoozonide of the corresponding olefine undergoes hydrogenation in a solution and in presence of a catalyst system comprising (A) a noble metal comprising palladium or platinum and carried on a carrier comprising alumina, coal or barium sulphate, and
(B) at least one compound of a heavy metal, and wherein, when a saturated dialdehyde is to be prepared, the unsaturated dialdehyde prepared as above undergoes a further catalytic hydrogenation in an organic solvent after removal of component (B) of the said system by means of a treatment with an ion-exchange resin acidified with sulphuric acid, the resin being of such quantity that the acid equivalents of the resin are at least equal to the equivalents of the heavy metal in the component (B) of said catalytic system.

16 Claims, No Drawings

PROCEDURE FOR THE PREPARATION OF SATURATED AND UNSATURATED DIALDEHYDES

The invention concerns a procedure for the preparation of saturated and unsaturated dialdehydes. To be more exact, this invention has as its object a procedure for the preparation of saturated and unsaturated α,ω-dialdehydes by catalytic reduction of the corresponding monoozonides of poly-unsaturated cycloolefines. The α,ω-dialdehydes thus obtained also constitute an object of this invention.

Diagrammatically the reaction is as follows:

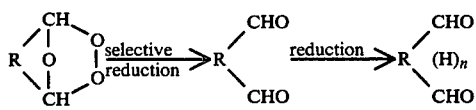

where R represents an olefine chain with one or more unsaturations, while $R(H)_n$ represents the corresponding paraffin chain.

Thus in its first phase the invention refers to the selective catalytic reduction of the "ozonide" group and not of the double bonds of the olefine chain, whereas in its second phase it refers to the reduction of the double bonds

Furthermore the invention concerns a method of obtaining high yields of unsaturated α,ω-dialdehydes whilst avoiding or minimizing undesired side reactions such as the formation of unsaturated acid α,ω-aldehyde.

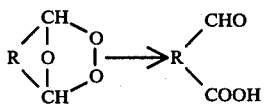

(R has the meaning explained previously).

The monoozonides of the poly-unsaturated cycloolefines can be obtained by the selective monoozonization in two solvents, one polar and the other non-polar, of the poly-unsaturated cycloolefines in accordance with the methodology described in Italian Pat. No. 998.227, for instance.

The selective reduction of the monoozonides to unsaturated dialdehyde can be carried out directly on the solution of the ozonide in the polar solvent as resulting from the reaction of monoozonization, where said polar solvent consists of one single solvent or else of a mixture of two or more solvents, such as acetic acid and acetic anhydride, for instance.

INDUSTRIAL IMPORTANCE OF THE PRODUCTS OF THE INVENTION

As far as is known in the present state of the art in question, the unsaturated and saturated α,ω-dialdehydes serve above all, for instance, as intermediates for the synethesis, by means of known procedures, of other products which in turn are compound intermediates (such as the corresponding diacids and diamines), from which the various types of nylon can then be obtained.

KNOWN METHODS OF OBTAINING UNSATURATED AND SATURATED α,ω-ALDEHYDES CONTAINING 8,10 or 12 CARBON ATOMS

Known methods of obtaining unsaturated α,ω-dialdehydes refer generally to preparations on a laboratory scale.

For instance in Bulletin Chem. Soc. Japan 36/II pages 1390-2 (1963) the preparation of dodecadiene -4,8-dial(1,12) for the treatment of cyclododecatriene, firstly with hydrogen peroxide and next with lead tetraacetate, is described.

The preparation of unsaturated dialdehydes is also known (Chem. Zentr. 1959/7631 and Chem. Zentr. 18, 1233 (1969)), again with laboratory scale methods, whereby the ozonides are readily reduced to dialdehydes in the presence of a metal, which is, however, used in a quantity that is at least stoichiometric and not catalytic. The method of Lycan and Adams (JACS 51,625 (1929) and JACS 65,752 (1943)), for instance is a typical method which we have applied to reduce the monoozonide of cyclododecatriene with an excess quantity of zinc powder in acetic acid, thereby obtaining high yields of dodecadiene-4,8-dial-(1,12).

However, by reducing catalytically the ozonides of the mono-unsaturated cycloolefines with hydrogen in the presence of a reduction catalyst (for instance, platinum, palladium, etc.), alongside the dialdehydes large quantities of acid aldehyde are also produced (as much as 30-40% in some cases). For example, in Du Pont patent (B.P. 709.450) in the reduction of the ozonide of cyclohexene (mono-unsaturated cycloolefine) to adipic dialdehyde the yields do not exceed 70%.

Next, to obtain unsaturated dialdehydes it is necessary that it should be possible to halt the hydrogenation as soon as the peroxide function disappears and also that the hydrogen should not be absorbed by the double bonds of the olefine chain as well (both these conditions are very difficult to control and regulate).

DESCRIPTION OF THE INVENTION

The Applicants have now discovered unexpectedly (and this constitutes one of the objects of this invention) that it is possible to obtain unsaturated α,ω-dialdehydes by carrying out reduction of the monoozonides of poly-unsaturated cycloolefines in a solution and in the presence of a catalyst system consisting of:

(A) a noble metal, either palladium or platinum, carried on calcium carbonate, alumina, coal, barium sulphate, etc. and (B) one or more compounds of a heavy metal such as lead, bismuth, etc.

The catalyst system (B) may be added to the solution of the ozonide with various procedures which depend mainly on the form in which said catalyst system exists; for instance, where the compound of the heavy metals is in the form of salts soluble in the solvent of the ozonide (for example, acetates), they are added direct to the solution, whereas where said compound is in the form of an oxide they are added to the reduction catalyst, which is generally a noble metal deposited on a carrier; lastly, a further procedure consists in impregnating the noble metal thus carried with a suitable solution of one or more of these salts of heavy metals.

The quantity of the catalyst system as employed in accordance with the invention is preferably as follows: the quantity by weight of component (A) is kept between 0.1% and 1% of the quantity of monoozonide, whereas the quantity of heavy metal may vary from 0.5 to 10 times the weight of the noble metal employed so that the reduction will stop at the unsaturated dialdehyde, in compliance with the invention, and will not act on the double olefine bonds as well.

The reduction temperature may vary from a very low temperature (the limit being the solidification of the solvents) up to more than 100° C. In practice it has been noted that it is not convenient to have too low a temperature, apart from the need for stability in the ozonide employed, since the reaction is slowed down too much; nor is too high a temperature convenient inasmuch as at high temperatures the unsaturated aldehydes tend to provide polymerization and condensation, even though no absorption of hydrogen on the double bonds has been noted up to 100° C. The best hydrogenation temperature generally varies, according to the invention, from 0° to 60° C., while the pressure varies from the ambient pressure up to 50 atmospheres.

The selective reduction of the poly-unsaturated cycloolefines to unsaturated dialdehydes may be carried out continuously or discontinuously, at the ambient pressure or under pressure; it is done discontinuously under pressure by loading into a steel autoclave the catalyst system and then the ozonide solution; it is done continuously by feeding all the components into the autoclave with suitable systems and complying with the batch times, which vary with the speed of hydrogenation of the ozonide; where necessary, in the latter of these two cases it is possible to use more than one autoclave in series so as to increase the degree of conversion of the ozonide to unsaturated dialdehyde.

When the solution does not absorb any more hydrogen, the pressure is released from the autoclave and the solid catalyst is filtered. This catalyst may be used again for further hydrogenation of unsaturated ozonides after the whole or part of component (B) of the catalyst system has been re-added.

A further object of this invention is to prepare saturated α,ω-dialdehydes by means of hydrogenation of the double olefine bonds of the corresponding unsaturated dialdehydes obtained as indicated in the foregoing text, for example.

Since the solution of the unsaturated dialdehyde still contains the compound of heavy metal, this latter must be removed before carrying out catalytic hydrogenation of the double bonds. This is done by treating the unsaturated dialdehyde in an organic solvent with an ion-exchange resin acidified with sulphuric acid (of the "Amberlite" type, for instance), the quantity being such that the acid equivalents of the resin are equal to or greater than the equivalents of the metal used as an inhibiting agent. The treatment is best carried out in an inert gas ($N_2$, $CO_2$, etc.) and may be effected at a temperature below 70° C. but is preferably done at the ambient temperature, the solution of dialdehyde and resin being stirred, or else the solution of the dialdehyde being made to percolate through the resin, which has been suitably predisposed in a column, for example. The solution of unsaturated dialdehyde is then placed in an autoclave in the presence of a hydrogenation catalyst such as palladium, platinum, rhodium, etc. and is hydrogenated at a pressure ranging from the ambient pressure up to 50 atmospheres and at a temperature from 0° up to 50° C. When absorption of hydrogen has ceased, the pressure in the autoclave is released, the solution is filtered to separate out the catalyst and the solvent is evaporated; the saturated dialdehyde is thus obtained.

The decationization treatment may also be followed by washing the unsaturated dialdehyde with water; in this case it is necessary to evaporate the organic solvent, which is generally miscible with water, and to carry out washing with water on the residue consisting of unsaturated dialdehyde; to increase the speed of separation of the aqueous and organic phases, the unsaturated dialdehyde may be dissolved in a solvent insoluble in water, such as benzol, toluol, xylol, carbon tetrachloride, chloroform, etc.

By washing the unsaturated dialdehyde with water a higher speed of hydrogenation of the double bonds is obtained than is the case with dialdehyde not washed with water. The following examples are for illustrative purposes but are not limitative.

EXAMPLE I

Reduction of the Monoozonide of Cyclododecatriene (CDT) to Dodecadiene-4,8-Dial-(1,12)

The monoozonide of cyclododecatriene was prepared with known methods, such as that described in Italian Pat. No. 998.227, by continuous ozonization of the CDT in a mixture of solvents consisting of acetic acid and petrolatum oil, which formed the stationary phase of the ozonization reactor. 340 g/hr of c,t,t,-1,5,9-cyclododecatriene, 100 g/hr of ozone and 1315 g/hr of acetic acid containing 5% of water were dosed. The ozonide solution separated out continuously, forming as an acetic solution still containing small quantities of unreacted cyclododecatriene and petrolatum oil, which were removed by extraction with cyclohexane. From the iodometric titre it was calculated that the solution contained 23.9% of ozonide of CDT.

In an 8-liter autoclave, which was stirred mechanically, there were placed under nitrogen 500 cc. of 95% acetic acid containing 1.91 g. of lead acetate trihydrate and 20 g. of palladium at 5% on alumina. The autoclave was washed with nitrogen and then with hydrogen, and lastly the hydrogen pressure was raised to 20 atmospheres at a temperature of 20° C. By means of a pump with pistons there were charged into the autoclave, at a rate of 1000 g/hr, 3890 g. of monoozonide of CDT in an acetic solution as obtained from the ozonization and extraction previously described. The temperature was kept at 25° C. by causing water at 15° C. to circulate in a stainless steel coil positioned within the autoclave.

The pressure stabilized at 10 atmospheres 30 minutes after completion of charging of the ozonide solution, whereafter it was left for a further 30 minutes at 20 atmospheres at 25° C. without any more absorption of hydrogen being noted.

The solution was discharged through a filter so as to retain the palladium catalyst, whereafter it was treated at the ambient temperature for 60 minutes with 10 cc. of wet "Amberlite" sulphonic resin.

The acetic solution of unsaturated dialdehyde thus obtained was then evaporated in a vacuum. The residue was washed with water to remove the last quantities of acetic acid and was then dried again in a vacuum.

961.58 g. of dialdehyde residue were thus obtained with the following analytical characteristics:

$CHO = 9.4$ meq/g $H+ = 0.53$ meq/g

Pure dodecadiene-4,8-dial-(1,12) is obtained by distillation of the product of reduction; the product boils at 101° C. in a vacuum of 0.07 mm. Hg. The distilled product has the following analysis:

| | |
|---|---|
| CHO = 10.16 meq/g | (10.3 theoretical) |
| H+ = 0.08 meq/g | (1 theoretical) |

The physical characteristics of this product are as follows:

| | |
|---|---|
| $n_{20}^D$ = 1.4789 | (1.4799 tabulated) |
| $D_{20}$ = 0.956 | (0.9625 tabulated) |

EXAMPLE 2

Reduction of the Monoozonide of CDT to Dodecadiene-4,8-Dial-(1,12). Solvent: Acetic Acid and Acetic Anhydride The monoozonide of CDT was prepared with known methods by ozonization of cyclododecatriene in a mixture of solvents consisting of petrolatum oil, acetic acid and acetic anhydride.

The monoozonide solution obtained by continuous ozonization was treated with cyclohexane to extract the small quantities of petrolatum oil and unreacted CDT present. After this treatment the solution had the following composition:

| | |
|---|---|
| monoozonide of CDT | 25.67% |
| acetic acid | 25.67% |
| acetic anhydride | 43.65% |
| cyclohexane | 5.0% |

Into the 8-liter autoclave described in Example I there were introduced 500 cc. of glacial acetic acid, 20 g. of a 10% solution of lead acetate trihydrate and 20 g. of palladium at 5% on an alumina carrier. The autoclave was filled with hydrogen, and at a temperature of 20° C. 3630 g. of the ozonide solution were pumped in at a rate of 1000 g/hr, the internal pressure of the autoclave being kept at 20 atmospheres.

When charging of the ozonide solution had been completed, the hydrogenation was continued for a further 30 minutes and then, when it had been verified that absorption of hydrogen had stopped, the product was discharged through a filter and was treated while being stirred for one hour with 10 cc. of "Amberlite" resin and was then evaporated to a thin film under a vacuum.

The remaining residue was dissolved in a little toluol, washed with water and evaporated once again to a thin film.

960.41 g. were thus obtained with characteristics of:
CHO=9.30 meq/g
H+ =0.64 meq/g

EXAMPLE 3

Reduction of the Monoozonide of Cyclooctadiene (COD) to Octen-4-Dial-(1,8)

The monoozonide of cyclooctadiene was prepared with known methods, in acetic acid and cyclohexane, from cyclooctadiene and ozone. 500 g. of the monoozonide solution thus obtained and having the following composition:

| | |
|---|---|
| monoozonide of COD | = 16.23% by weight |
| acetic acid | = 73.77% by weight |
| water | = 5.0% by weight |
| cyclohexane | = 5.0% by weight | were introduced together with 0.238 g. of lead acetate trihydrate and 2.5 g. of palladium at 5% on a carrier of coal into a autoclave that was constantly stirred.

The hydrogenation of the peroxide group was carried out at 10° C. under a pressure of 5 atmospheres of hydrogen. When absorption of hydrogen had stopped and the catalyst had been removed by filtration, the solution was treated at 10° C. for 1 hour with 2 cc. of "Amberlite IR 120" ion-exchange resin. The residue was removed by filtration and the solvent was evaporated to a thin film under a vacuum, thus providing 73.5 g. (72.8 theoretical) of a residue having the following analytical characteristics:

| | |
|---|---|
| acidity | meq/g) 0.87 |
| aldehydes | meq/g) 13.4 |
| double bonds | (m moles of $H_2$/g) 7.2 |

EXAMPLES 4 TO 16 INCLUSIVE

Examples 4 to 16 inclusive are examples for comparative purposes. In more detail, examples 4 and 5 were carried out by reducing the monoozonide of CDT with zinc powder; this system pre-supposes a heavy consumption of reagent but is known in this art to be one of the most efficient means for reducing ozonides to dialdehydes.

In Example 6 the ozonide was reduced with hydrogen by using palladium carried on alumina as a catalyst, namely a traditional reduction catalyst. As can be seen, the percentage of dodecadiene-4,8-dial-(1,12) obtained is negligible.

In Examples 7 to 11 inclusive various types of compound catalysts were employed. Out of all of them, only the use of $PtO_2$ and $Zn(CH_3COO)_2$, and $PtO_2$ and DMSO (dimethylsulphoxide) provided a satisfactory yield of unsaturated dialdehyde-12. Examples 12 to 16 inclusive were carried out with palladium catalysts in the presence of variable quantities of lead acetate to establish the efficiency of lead acetate in various proportions. All these data have been collected in Table I, wherein ACAC is acetic acid.

TABLE No. I

| Example n | Catalyst | % on prod. | solvent | Temp. °C. | Press Atm. | Mins. | $H_2$ absorbed moles $H_2$/ moles ozonide | Product obtained (dodecadiene-4, 4,8-dial-1, 1,12)moles per 100 moles of monoozonide of CDT) |
|---|---|---|---|---|---|---|---|---|
| 4 | Zn powder | 100 | EtOH | 0 | amb. | — | not determ- | 90.5% |

TABLE No. I-continued

| Example n | Catalyst | % on prod. | Conditions solvent | Temp. °C. | Press Atm. | Mins. | H₂ absorbed moles H₂/ moles ozonide | Product obtained (dodecadiene-4,8-dial-1,1,12) moles per 100 moles of monoozonide of CDT) |
|---|---|---|---|---|---|---|---|---|
| 5 | Zn powder | 80 | H₂O EtOH— H₂O | 5 | amb. | — | inable not determ. | 89.4% |
| 6 | Pd 5% on Al₂O₃ | 5 | AC AC | 22 | amb. | 115' | 3.4 | 3.4% |
| 7 | PtO₂ + FeSO₄ | 2 + 2 | AC AC | 24 | amb. | 155' | 1.55 | 8.6% |
| 8 | PtO₂ + Zn(CH₃COO)₂ | 4 + 16 | AC AC | 27 | amb. | 60' | 1.23 | 64.9% |
| 9 | Pt 5% on C + Zn(CH₃COO)₂ | 4 + 16 | AC AC | 28 | amb. | 85' | 0.7 | 47.1% |
| 10 | PtO₂ + DMSO | 2 + 30 | AC AC | 21 | amb. | 375' | 1.84 | 61.4% |
| 11 | Pd 5% on Al₂O₃ + DMSO | 2 + 30 | AC AC | 21 | amb. | 2004' | 1.34 | 50.5% |
| 12 | Pd 5% on Al₂O₃ + Pb(CH₃COO)₂ | 20 + 30 | AC AC | 20 | amb. | 60' | 1.06 | 92.9% |
| 13 | Pd 5% on C + Pb(CH₃COO)₂ | 20 + 10 | AC AC | 20 | amb. | 60' | 1.06 | 92.1% |
| 14 | Pd 5% on C + Pb(CH₃COO)₂ | 20 + 3 | AC AC | 20 | amb. | 60' | 1 | 86.6% |
| 15 | Pd 5% on C + Pb(CH₃COO)₂ | 20 + 1 | AC AC | 20 | amb. | 60' | 0.97 | 85% |
| 16 | Pd 5% on C + Pb(CH₃COO)₂ | 20 + 0.25 | AC AC | 20 | amb. | 130' | 1.7 | 50.5% |

EXAMPLES 17 AND 18

Parallel with the tests shown in Examples 4 to 16 inclusive, poisonous metals besides lead were also tested. Cadmium was found to be particularly efficient, antimony being slightly less so, as can be seen in:

TABLE No. 2

| No. | Catalyst | % on product | solvent | Temp. °C. | Press. | Mins. | H₂ absorbed | Product obtained % |
|---|---|---|---|---|---|---|---|---|
| 17 | Pd/Al₂O₃ + Cd(CH₂COO)₂ . H₂O | 4 + 0.50 | AC . AC 85% | 27 | Amb. | 240' | 1.51 | 89.0% |
| 18 | Pd/Al₂O₃ + Sb₂O₃ | 4 + 0.27 | AC . AC 85% | 30 | Amb. | 90' | 1.28 | 84.5% |

EXAMPLE 19

Reduction of Dodecadiene-4,8-Dial-(1,12) to Dodecanedial-(1,12)

150.4 g. of distilled dodecadiene-4,8-dial-(1,12) (groups CHO 10.15 meq/g; groups COOH 0.12 meq/g; double bonds 10.15 meq/g) were dissolved in 350 cc. of methyl alcohol. The solution was placed in an autoclave and hydrogenated at 4 Atms. of H₂ at a temperature of 20°–30° C. in the presence of 3.5 g. of palladium at 5% on alumina. The discharge from the autoclave was filtered and kept at 0° C. After one night 134.5 g. of dodecanedial-(1,12) were precipitated (Melting Point 36°–38° C. groups CHO=9.94 meq/g; groups COOH=0.092 meq/g; double bonds=traces).

We claim:

1. A method for the preparation of unsaturated α,ω-dialdehydes of the formula:

where R represents an olefin chain having one or more unsaturations, comprising selectively hydrogenating the monoozonide of the polyunsaturated cycloolefin represented by the formula:

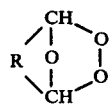

in a polar solvent solution at a temperature from the freezing point of said solvent to 100° C. with excess hydrogen gas at a pressure from ambient to 50 atmospheres in the presence of a catalyst system comprising:

(A) 0.1 to 1 percent by weight based on said monoozonide of a noble metal selected from the group consisting of palladium and platinum and carried on a carrier selected from the group consisting of alumina, coal, and barium sulphate, and (B) 0.5 to 10 times the weight of said noble metal of at least one compound of a heavy metal selected from the group consisting of lead, bismuth, cadmium, and antimony, until no more hydrogen is taken up, whereby only the peroxide function of said monoozonide of a poly-unsaturated cycloolefin is hydrogenated, thereby leaving the double bonds unaffected.

2. A method according to claim 1 wherein component (B) of the catalyst system is added directly to the solution in the form of a salt soluble in the solvent of the ozonide.

3. A method according to claim 1, wherein component (B) of the catalyst system is used in the form of an oxide.

4. A method according to claim 1, wherein component (A) of the catalyst system is impregnated with a solution of component (B) of said system.

5. A method according to claim 1, wherein a compound of lead, bismuth or cadmium is employed as the compound of a heavy metal.

6. A method according to claim 1, carried out at a temperature between 0° and 60° C. and at a pressure between 1 and 50 atmospheres.

7. Unsaturated α,ω-aldehydes obtained according to the method of claim 1.

8. A method according to claim 1, wherein said polar solvent is acetic acid, acetic anhydride, mixtures thereof, or a mixture of ethanol and water.

9. A method according to claim 1, wherein said α,ω-dialdehyde and said monoozonide of a cycloolefin each have from 8 to 12 carbon atoms.

10. A method according to claim 1, for the preparation of saturated α,ω-dialdehydes of the formula:

wherein R(H)n represents the paraffin chain corresponding to R, further comprising:
(a) removing said one or more compounds of a heavy metal by passing the resulting mixture from the selective hydrogenation step through an ion-exchange resin acidified with sulphuric acid, said resin being in such amount that the acid equivalence of the resin is at least equal to the equivalence of the heavy metal; and
(b) hydrogenating said unsaturated α,ω-dialdehyde in an organic solvent in the presence of a catalyst system comprising component (A) at a temperature from 0° to 50° C. with excess hydrogen gas at a pressure from ambient to 50 atmospheres until no more hydrogen is taken up.

11. A method according to claim 10, wherein hydrogenation of the unsaturated aldehyde to the saturated aldehyde is carried out in the presence of a catalyst chosen from among palladium, platinum or rhodium.

12. A method according to claim 10, wherein, before undergoing hydrogenation, the unsaturated dialdehyde is washed with water.

13. Saturated α,ω-dialdehydes obtained according to the method of claim 10.

14. A method for the preparation of unsaturated α,ω-dialdehydes represented by the formula:

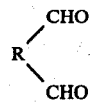

where R represents an olefin chain having one or more unsaturations, comprising:
(A) ozonizing a poly-unsaturated cycloolefin in a polar solvent to form the monoozonide of said cycloolefin represented by the formula:

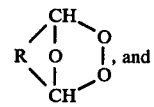

(B) selectively hydrogenating said monoozonide of said poly-unsaturated cycloolefin in the same solvent at a temperature of from the freezing point of said solvent to 100° C. with excess hydrogen gas at a pressure of from ambient to 50 atmospheres in the presence of a catalyst system comprising
(1) 0.1 to 1% by weight based on said monoozonide of a noble metal selected from the group consisting of palladium and platinum and carried on a carrier selected from the group consisting of alumina, coal, and barium sulphate, and
(2) 0.5 to 10 times the weight of said noble metal of at least one compound of a heavy metal selected from the group consisting of lead, bismuth, cadmium, and antimony, until no more hydrogen is taken up, whereby only the peroxide function of said monoozonide of a poly-unsaturated cycloolefin is hydrogenated, thereby leaving the double bonds unaffected.

15. A method for the preparation of α,ω-dialdehydes represented by the formula:

wherein R represents an olefin chain having one or more unsaturations comprising:
(a) selectively hydrogenating the monoozonide of a poly-unsaturated cycloolefin represented by the formula:

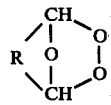

in a polar solvent solution at a temperature from the freezing point of said solvent to 100° C. with excess hydrogen gas at a pressure from ambient to 50 atmospheres in the presence of a catalyst system comprising
(A) 0.1 to 1 percent by weight based on said monoozonide of a noble metal selected from the group consisting of palladium and platinum and carried on a carrier selected from the group consisting of alumina, coal, and barium sulphate, and
(B) 0.5 to 10 times the weight of said noble metal of at least one compound of a heavy metal selected from the group consisting of lead, bismuth, cadmium, and antimony, until no more hydrogen is taken up, whereby the peroxide function of said monoozonide of the poly-unsaturated cycloolefin is hydrogenated to produce the unsaturated α,ω-dialdehydes of the formula:

16. A method for the preparation of an α,ω-dialdehyde from monoozonides of poly-unsaturated cycloolefins of the formula

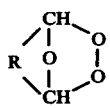

wherein R represents an olefin chain having one or more unsaturations which comprises:
(a) selectively hydrogenating the monoozonide of a polyunsaturated cycloolefin represented by the formula:

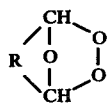

in a polar solvent solution at a temperature from the freezing point of said solvent to 100° C. with excess hydrogen gas at a pressure from ambient to 50 atmospheres in the presence of a catalyst system comprising
(A) 0.1 to 1 percent by weight based on said monoozonide of a noble metal selected from the group consisting of palladium and platinum and carried on a carrier selected from the group consisting of alumina, coal, and barium sulphate, and
(B) 0.5 to 10 times the weight of said noble metal of at least one compound of a heavy metal selected from the group consisting of lead, bismuth, cadmium, and antimony, until no more hydrogen is taken up, whereby only the peroxide function of said monoozonide of said poly-unsaturated cycloolefin is hydrogenated to produce an unsaturated α,ω-dialdehyde of the formula:

removing said one or more compounds of a heavy metal by passing the resulting mixture from step (a) through an ion-exchange resin acidified with sulphuric acid, said resin being in such amount that the acid equivalence of the resin is at least equal to the equivalence of the heavy metal, and hydrogenating said unsaturated α,ω-dialdehyde in an organic solvent in the presence of a catalyst system comprising component (A) at a temperature from 0° to 50° C. with excess hydrogen at a pressure from ambient to 50 atmospheres until no more hydrogen is taken up, to produce a saturated α,ω-dialdehyde of the formula

wherein n is an integer equal to the number of unsaturations in said olefin chain.

* * * * *

UNITED STATES PATENT OFFICE
CERTIFICATE OF CORRECTION

Patent No. 4,177,214      Dated December 4, 1979

Inventor(s) Francesco Siclari, et al

It is certified that error appears in the above-identified patent and that said Letters Patent are hereby corrected as shown below:

Column 3, line 24: after "the" (2nd occurrence) insert
--monoozonides of the--.

Columns 5 & 6 - Table No. 1: last column in table
"(dodecadiene-4,4,8-dial-1,1,12) moles" should be
--(dodecadiene-4,8-dial-1,12) moles--.

Columns 7 & 8 - Table No. 1 - continued: last column in table
"(dodecadiene-4,4,8-dial-1,1,12) moles" should be
--(dodecadiene-4,8-dial-1,12)moles--.

Signed and Sealed this

Eighth Day of July 1980

[SEAL]

Attest:

SIDNEY A. DIAMOND

Attesting Officer      Commissioner of Patents and Trademarks